(12) United States Patent
Kallback et al.

(10) Patent No.: US 8,286,663 B2
(45) Date of Patent: Oct. 16, 2012

(54) RANDOM ACCESS ROTARY VALVE

(75) Inventors: Patrik Kallback, Uppsala (SE); Anders Wilen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 532 days.

(21) Appl. No.: 12/597,762

(22) PCT Filed: May 8, 2008

(86) PCT No.: PCT/SE2008/000317
§ 371 (c)(1),
(2), (4) Date: Oct. 27, 2009

(87) PCT Pub. No.: WO2008/140377
PCT Pub. Date: Nov. 20, 2008

(65) Prior Publication Data
US 2010/0127200 A1 May 27, 2010

(30) Foreign Application Priority Data
May 15, 2007 (SE) .................................. 0701220

(51) Int. Cl.
*F16K 11/06* (2006.01)
(52) U.S. Cl. ................. 137/625.15; 73/863.72

(58) Field of Classification Search .............. 137/625.15, 137/625.46; 73/61.55, 61.56, 863.72, 864.83
See application file for complete search history.

(56) References Cited

U.S. PATENT DOCUMENTS

| | | | | |
|---|---|---|---|---|
| 3,140,615 A | * | 7/1964 | Broerman | .................. 73/863.71 |
| 3,411,525 A | | 11/1968 | Auger | |
| 3,796,232 A | * | 3/1974 | Dalton | ...................... 137/625.21 |
| 4,068,528 A | * | 1/1978 | Gundelfinger | .............. 73/864.84 |
| 4,625,569 A | * | 12/1986 | Toei et al. | .................. 73/863.72 |
| 5,601,115 A | | 2/1997 | Broerman | |
| 5,803,117 A | | 9/1998 | Olsen et al. | |
| 6,012,487 A | * | 1/2000 | Hauck | ...................... 137/625.11 |
| 6,012,488 A | * | 1/2000 | Nichols | .................... 137/625.11 |
| 6,155,123 A | | 12/2000 | Bakalyar | |
| 6,550,496 B2 | * | 4/2003 | Tiemann et al. | ......... 137/625.46 |
| 6,672,336 B2 | | 1/2004 | Nichols | |
| 7,503,203 B2 | * | 3/2009 | Gamache et al. | ............ 73/23.42 |

* cited by examiner

*Primary Examiner* — John Fox

(57) ABSTRACT

A rotary valve for selectively connecting at least one component (51, 52) into a fluid path. According to the invention the inner stator face (111a, 211a) comprises orifices (131b-136b; 231b-236b) and said inner rotor face (112a, 212a) comprises at least a first groove (121, 221), a second groove (122, 222), and a third groove (123, 223) so arranged that the rotary valve can take at least three different rotary positions, in which either both components are bypassed, only one of the components is connected and the other bypassed or both components are connected to a main flow.

6 Claims, 8 Drawing Sheets

RANDOM ACCESS ROTARY VALVE

CROSS-REFERENCE TO RELATED APPLICATIONS

This application is a filing under 35 U.S.C. §371 and claims priority to international patent application number PCT/SE2008/000317 filed May 8, 2008, published on Nov. 20, 2008, as WO 2008/140377, which claims priority to patent application number 0701220-6 filed in Sweden on May 15, 2007.

FIELD OF THE INVENTION

The present invention relates to valves and more specifically to rotary valves for selectively enabling components into a main flow.

BACKGROUND OF THE INVENTION

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotator with respect to the stator.

Rotary valves can be designed to withstand high pressures (such as pressures above 30 MPa). They can be made from a range of materials, such as stainless steel, high performance polymeric materials and ceramics.

The number of inlets/outlets as well as the design of grooves in the rotor or the stator reflects the intended use of a specific valve.

A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

More complicated arrangements, tailor-made to perform one or several specific tasks, are possible. For instance, rotary valves may be used to introduce a fluid sample into the fluid path of an analytical system.

For example, a rotary valve that allows the user to independently of each other control a first flow to either of a set of two outlets, and a second flow to either of a set of another two outlets is described in U.S. Pat. No. 6,672,336 to Nichols.

In many instruments handling a flow of a liquid, such as liquid chromatography systems (LCS), there is sometimes a need to be able to either include or to bypass a component. This situation is easily solved with a conventional 4-way double-path valve, schematically shown in FIGS. 1 and 2.

FIG. 3 shows two components, each connected to a flow path via a conventional 4-way double-path valve. Thus, one or both of the components can be disconnected from the flow.

However, it would be beneficial to be able to integrate the possibility to disconnect at least one of two components from the flow path into a single valve. One reason for this would be to save cost (e.g. since there is need for one valve motor drive only in the case of an automatically operated valve). Another reason would be the possibility to shorten path lengths by integrating as much paths into the valve as possible, thereby reducing the need for interconnecting tubing.

It would be additionally beneficial if such a valve should include even more functionality, such as the possibility to flush one of the components using a second liquid source. For instance, this would be the case if one of the components requires calibration using a well defined calibration liquid. It would then be useful if this liquid (especially if it is expensive) could be introduced directly (e.g. with a syringe) to the component without the need to have it to pass the entire instrument.

Thus, there is a need for a multipurpose valve that allows at least one of two components to be independently connected to/disconnected from a main flow.

BRIEF DESCRIPTION OF THE INVENTION

This is achieved in a valve according to claim 1 of the present application.

Hereby one single rotary valve is achieved which can take at least three different rotary positions, in which either both components are bypassed, only one of the components is connected and the other bypassed or both components are connected to a main flow. This will both give a cheaper valve compared to using two separate valves and minimize interconnecting tubings.

Suitable embodiments are described in the dependent claims.

DETAILED DESCRIPTION OF THE INVENTION

Figure 1:
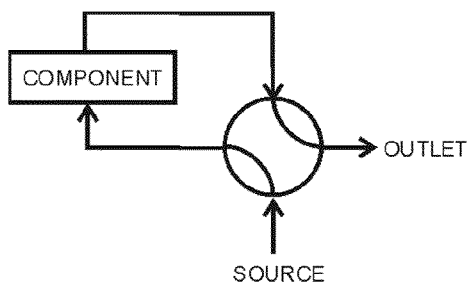
FIG. 1 shows flow through a component using a conventional valve in a first mode.
Figure 2:
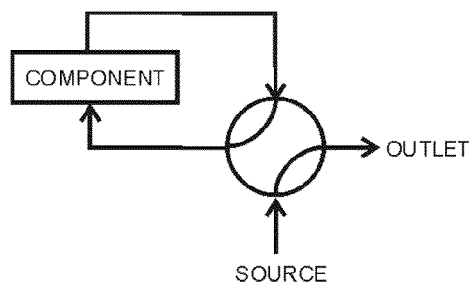
FIG. 2 shows bypassing the component of FIG. 1 using a conventional valve in a second mode.
Figure 3:
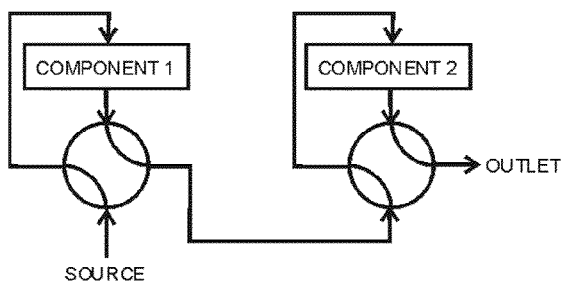
FIG. 3 shows two components connected to a flow path using two conventional valves.
Figure 4:
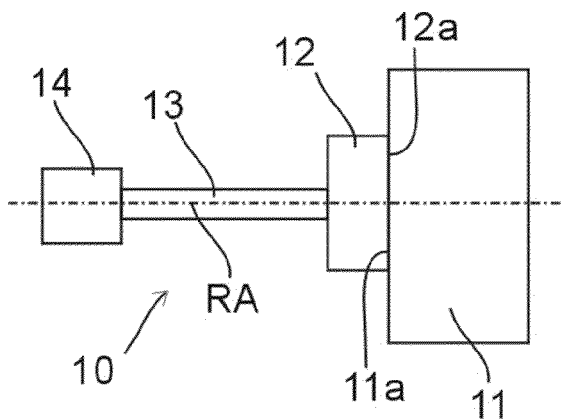
FIG. 4 is a schematic side view of a rotary valve.

The main parts of a typical rotary valve are schematically shown in FIG. 4 (wherein no brackets or similar load carrying or fastening elements are shown). The rotary valve 10 has a stator 11, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 11, which is fixed with respect to the instrument into which it is built, is provided with ports (not shown in FIG. 4) for fluid communication with a fluid source and any components with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of orifices on an inner stator face 11a, i.e. that surface of the stator that during operation is in contact with the rotor 12.

The rotor 12 is typically formed as a disc and has an inner rotor face 12a that is that face that is pressed against the inner stator face 11a during operation. The inner rotor face 12a is provided with one or more grooves which interconnect different orifices of the inner stator face 11a depending on the rotary position of the rotor with respect to the stator.

Figure 5:
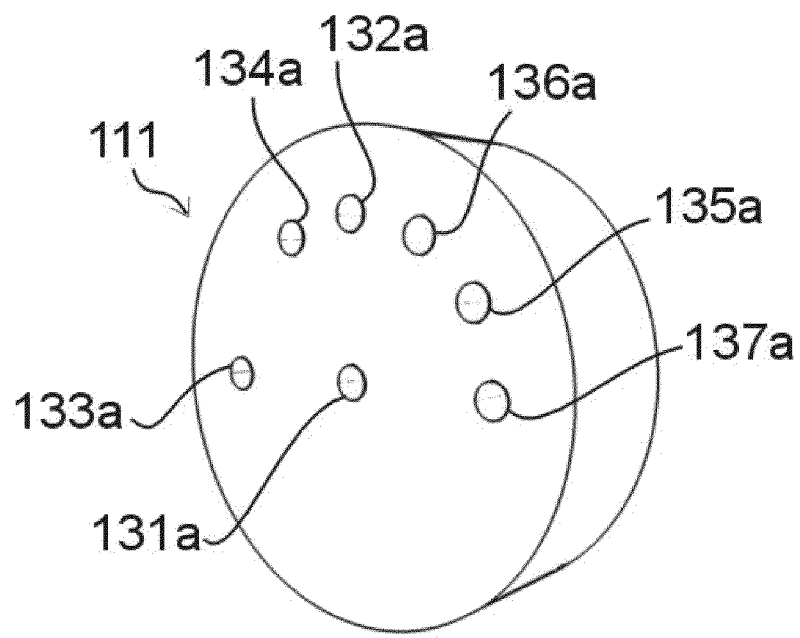
FIG. 5 is a perspective view of a stator of a first embodiment of the invention.

FIG. 5, which shows a simplified perspective view of the front side of a stator 111, illustrates the inlet and outlet port arrangement for a first embodiment of a valve according to the present invention.

Generally, it should be noticed that the angular position of ports, grooves and similar shown in the figures of the present application could differ between different embodiments of the invention, i.e. they could be turned with respect to the rotary axis of the valve, mirrored or altered in other ways as long as their mutual co-operation is still according to the inventive idea.

In addition, since the inlet/outlet ports are connected to orifices on the inner stator face 11a via bores (or any type of channels) it is possible to arrange the ports in a way that differs from the pattern on the inner stator face 11a by making non-linear channels between the ports and the orifices. However, for reasons of simplicity, the ports are shown as being positioned in-line with the inner stator face orifices, as will be described below in relation to FIG. 6.

Thus, the stator 111 of a first embodiment according to the present invention has seven ports 131a-137a that are used to connect the valve to all desired operative components of the instrument.

A first port 131a is a central port used as inlet port from a first liquid source of the instrument, such as a pump, typically via a set of components of the instrument such as detectors, other valves etc., and any connected components such as a chromatography column. A second port 132a serves as an outlet port from which the liquid is allowed to exit to the remaining part of the instrument or out from the instrument.

A first component, such as a conductivity monitor or a flow restrictor device, is connectable to the valve via a third port 133a and a fourth port 134a, whereby the third port 133a acts as an outlet from the valve and the fourth port 134a as an inlet to the valve for the returning flow.

A second component, such as a pH monitoring sensor, is connectable to the valve via a fifth port 135a and a sixth port 136a whereby the fifth port 135a acts as an outlet from the valve and the sixth port 136a as an inlet to the valve for the returning flow.

A seventh port 137a is an inlet that allows a second fluid source (such as a syringe) to be connected. This is, for instance, useful as a means for manual flushing of the second component, as is shown below. It should be noted that the seventh port 137a is optional, i.e. it could be omitted if the flushing feature is not of interest.

Figure 6:
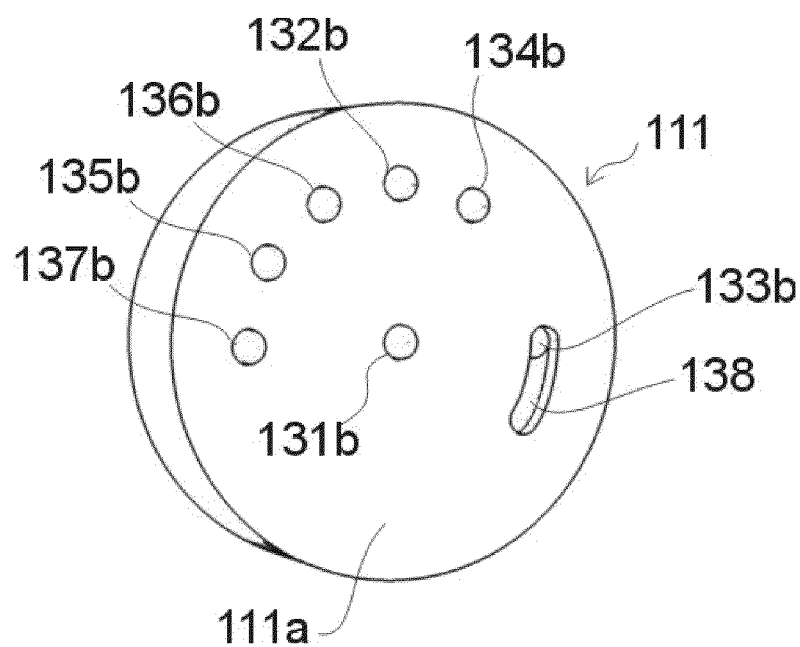
FIG. 6 shows the stator of FIG. 5 from the inner stator face side.

FIG. 6 is a perspective view of the stator 111 of FIG. 5 viewed from the other side, i.e. the inner stator face side 111a. Note that each port is connected to the inner stator face 111a via a channel ending in a corresponding orifice, a first orifice 131b, a second orifice 132b, a third orifice 133b, a fourth orifice 134b, a fifth orifice 135b, a sixth orifice 136b and optionally a seventh orifice 137b shown in FIG. 6.

In addition to the orifices connected to the ports, a stator groove 138 is provided in the inner stator face 111a. The groove is typically of essentially the same width as an orifice diameter. The orifice third 133b is situated inside the stator groove 138.

Figure 7:
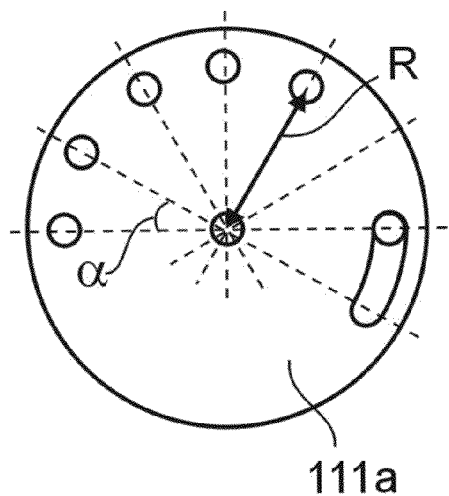
FIG. 7 illustrates the angular distribution of the orifices in the inner stator face of the stator according to FIG. 5

Looking at the inner stator face 111a, the general angular distribution of the orifices and the groove ends is illustrated in FIG. 7. The positions for orifices, groove ends (and not used positions) are equally distributed around the center of the stator (which center coincides with the rotary axis of the valve). As described above the positions of the orifices can be varied slightly without departing from the inventive idea. Since there are twelve such positions on the stator according to the embodiment, the partition angle α is 30°. All these positions are placed with essentially the same radial distance R to the rotational axis of the valve.

Figure 8:
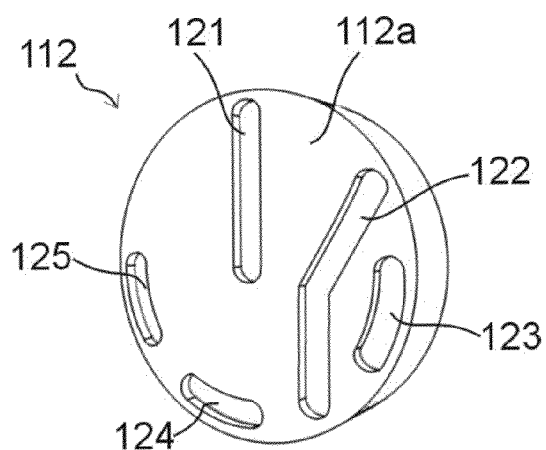
FIG. 8 is a perspective view of a rotor of the first embodiment of the invention.
Figure 9:
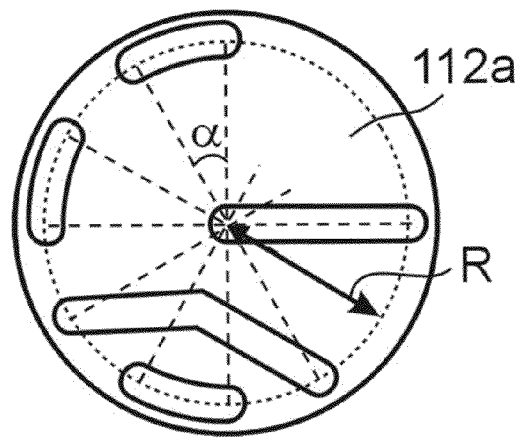
FIG. 9 illustrates the angular distribution of the grooves of the inner rotor face of the rotor according to FIG. 8.

The inner rotor face 112a of a rotor 112 of a first embodiment of the invention for cooperation with the stator 111 above is shown in FIG. 8. It is provided with five grooves, called the first, second, third, fourth and fifth groove 121-125, respectively. However, the fourth and fifth grooves 124, 125 are optional and not necessary for the invention as will be further described below. The mutual positions and shapes of the grooves are more clearly illustrated in FIG. 9.

Each rotor groove has both its ends ending essentially at the same radial distance R from the center, except for one end of the first groove 121 that ends in the center of the inner rotor face 112a (coinciding with the rotary axis of the valve). Of course, the radial distance R for the rotor is the same as the corresponding radial distance R of the stator. The first groove 121 is a straight groove from the center of the rotor face out towards the rim, with a length of R, and is parted from the nearest end of the second groove 122 by the angle 2α. The second groove 122, that extends over an angle of 3α, is bent inwards toward the centre to form a knee (or alternatively in an arcuate shape), thereby giving place for the third groove 123 that extends the angle α tangentially. The fourth and fifth grooves 124 and 125 each extend over an angle α. The angle α is in the present embodiment 30°. The fourth and fifth grooves 124 and 125 are mutually separated by the angle α. The fourth groove 124 is separated from the second groove 122, also with the angle α.

When assembled, the inner rotor face 112a is pressed against the inner stator face 111a in a manner that is typical for any conventional rotary valve (which is well known for anyone skilled in the art, and will not be explained herein). Depending on the mutual angular positions of the rotor 112 and the stator 111 different operation modes are obtained for the valve. These are illustrated in FIG. 10-13, wherein the grooves of the rotor are indicated by thick lines.

Figure 10:
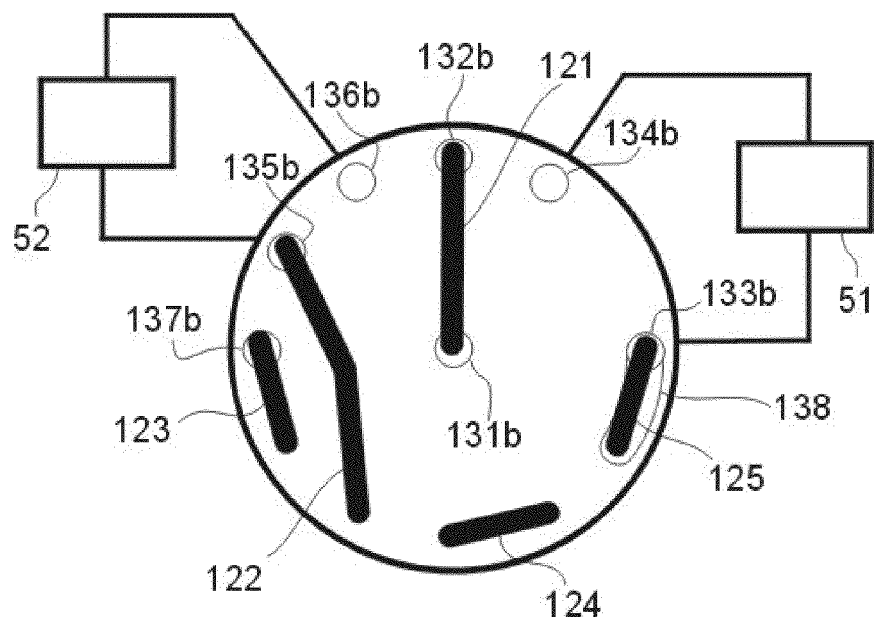
FIG. 10 is a schematic view of the first embodiment of the invention in a first position.

In the first rotary position of the rotor of the first valve embodiment, as shown in FIG. 10, the valve is useful to bypass both a first component 51 and a second component 52. The flow enters the first port 131a, goes via the first orifice 131b through the first rotor groove 121 and exits the valve through the second port 132a (via the second orifice 132b).

The other ports and grooves of the valve are not active in the first rotary position, i.e. both the first and the second components 51, 52 are bypassed.

Figure 11:
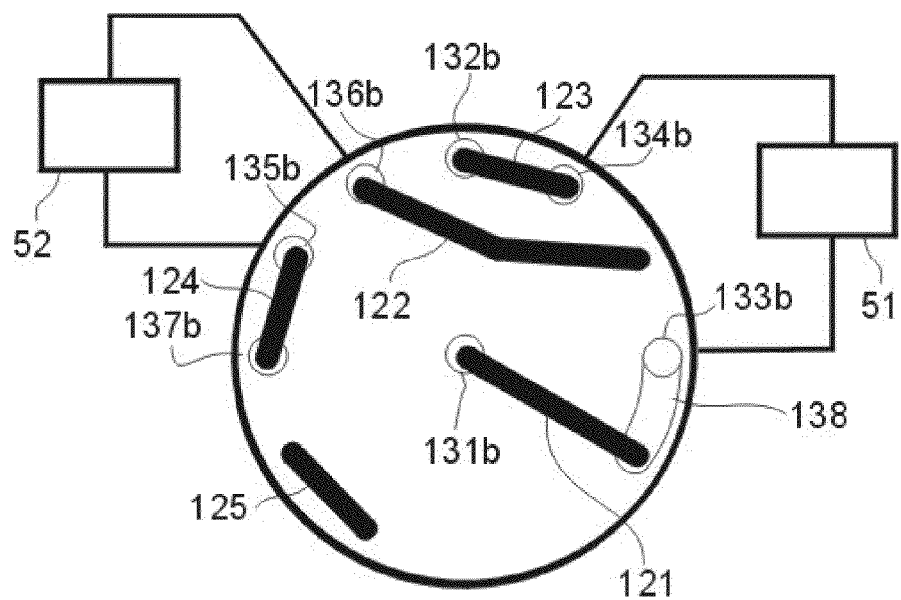
FIG. 11 is a schematic view of the first embodiment of the invention in a second position.

The second rotary position, as shown in FIG. 11, is obtained by rotating the rotor an angle of 4α clockwise (as seen from the view of FIG. 11) with respect to the first rotary position. The second position is useful to bypass the second component 52.

In the second rotary position the fluid that enters the first port 131a and the first orifice 131b will pass through the first rotor groove 121 and then the stator groove 138 to exit to the first component 51 via the third orifice 133b and the third port 133a. After passing the first component 51, the flow returns to the valve via the fourth port 134, passes the third rotor groove 123 and then exits the valve via the second port 132.

The other ports and grooves of the valve are not active in the second rotary position, i.e. the second component 52 is bypassed.

Figure 12:
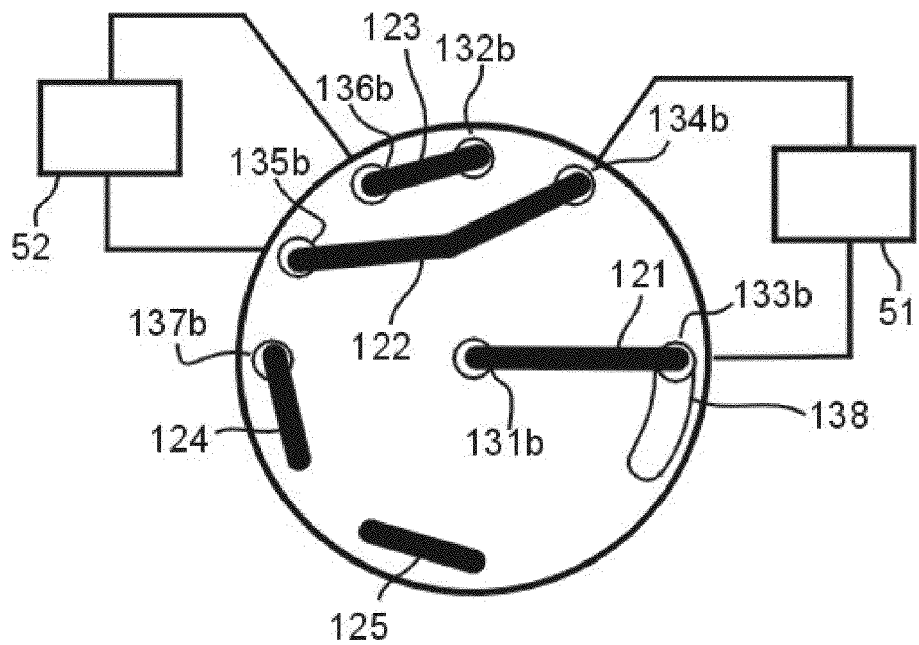
FIG. 12 is a schematic view of the first embodiment of the invention in a third position.

The third rotary position, as shown in FIG. 12, is obtained by rotating the rotor an angle of α counterclockwise (as seen from the view of FIG. 12) with respect to the second rotary position. In this position, the flow passes both the first and the second components 51, 52.

In the third rotary position, the fluid enters the first port 131a and the first orifice 131b and passes through the first groove 121 to exit to the first component 51 via the third orifice 133b and the third port 133a. In this case, the stator groove 138 forms a short cul-de-sac that can be rinsed when the rotor is set to the second rotary position. After passing the first component 51, the flow returns to the valve via the fourth port 134a and the fourth orifice 134b, passes the second rotor groove 122 and then exits to the second components 52 via the fifth orifice 135b and the fifth port 135a. After having passed the second component 52, the flow returns to the valve via the sixth port 136a and the sixth orifice 136b, passes the third groove 123 and then exits the valve via the second orifice 132b and the second port 132a.

The other ports and grooves of the valve are not active in the third rotary position.

Figure 13:
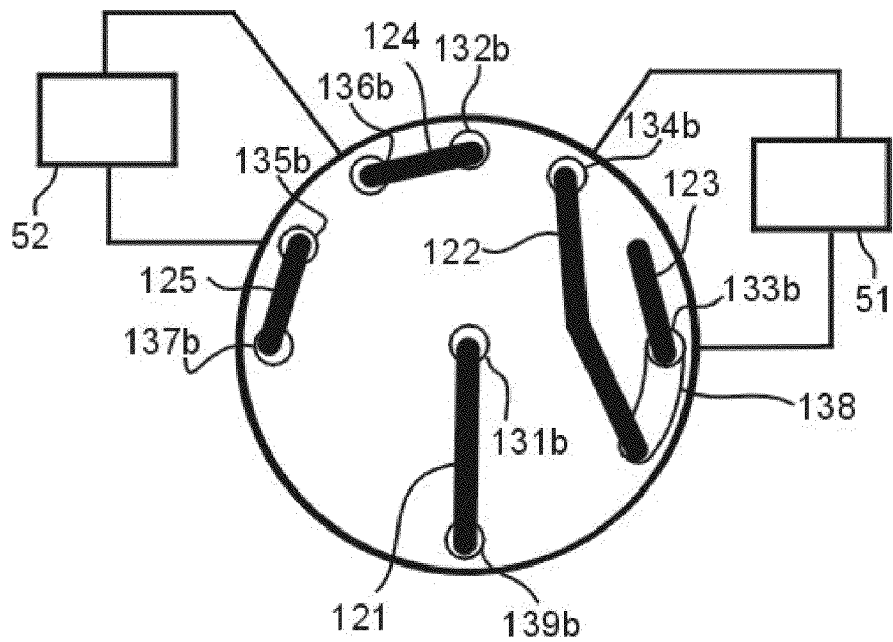
FIG. 13 is a schematic view of the first embodiment of the invention in a fourth position.

The fourth rotary position, as shown in FIG. 13, is obtained by rotating the rotor an angle 2α clockwise (as seen from the view of FIG. 13) with respect to the second rotary position. This position, that is optional, is useful for manual rinsing of the second component 52 (such as during a calibration procedure for the second component 52 or for cleaning purpose).

In the fourth rotary position, a fluid is entered via the seventh port 137a and the seventh orifice 137b, for example by using a syringe connected to the port. The fluid passes the fifth rotor groove 125 to exit to the second component 52 via the fifth orifice 135b and the fifth port 135a. After having passed the second component 52, the flow returns to the valve via the sixth port 136a and the sixth orifice 136b, passes the third groove 123 and then exits the valve via the second orifice 132b and the second port 132a.

The other ports and grooves of the valve are not active in the fourth rotary position, i.e. the first component 51 is bypassed.

It should be noted that in this fourth position, without an additional outlet orifice the first rotor groove 121 forms a stop for any flow from the fluid source via the first orifice 131b. In a modification of the first valve embodiment, an additional outlet orifice 139b (and corresponding additional outlet port) could be provided at a position corresponding to the outer end of the first groove 121 in this forth position to provide an outlet for the flow from said fluid source. The additional outlet orifice 139b is shown in FIG. 13. However this additional orifice is optional and not necessary for the invention.

Thus, with a valve of the first embodiment it is possible to selectively bypass the valve, connect the first component 51 in-line while bypassing the second component 52, or connect the first and second components 51, 52 (in said order) in-line. In addition an optional flushing position in provided.

Figure 14:
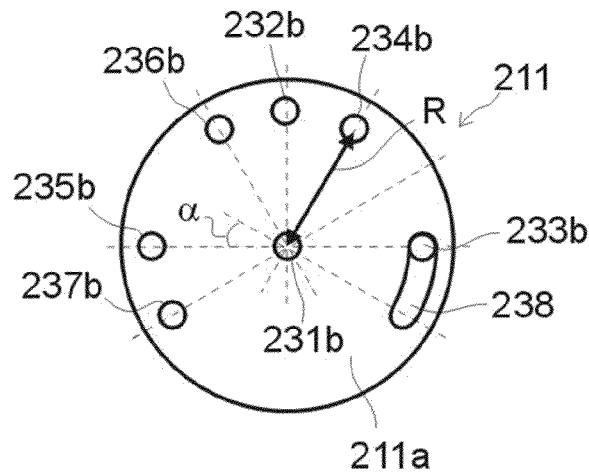
FIG. 14 is a schematic view of the inner stator face of a second embodiment of the invention.
Figure 15:
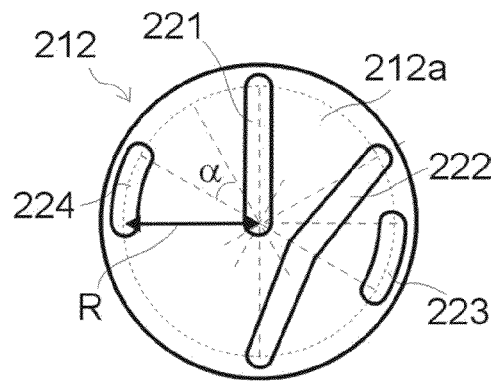
FIG. 15 is a schematic view of the inner rotor face of the second embodiment of the invention.

A rotor 212 and stator 211 design of a second embodiment of a valve according to the present invention are shown in FIGS. 14 and 15.

An inner stator face 211a of a stator 211 of the second embodiment is shown in FIG. 14. The shown orifices 231b-237b are in communication with connecting ports (not shown for this embodiment) in the same way as is described above for the first embodiment.

The inner stator face 211a of the stator 211 is similar to the inner stator face 111a of the first embodiment in that it is provided with a first orifice 231b that is a central inlet, a second orifice 232b that is an outlet, a third orifice 233b that is an outlet to a first component and a fourth orifice 234b that is an inlet from said first component, a fifth orifice 235b that is an outlet to a second component and a sixth orifice 236b that is an inlet from said second component, an optional seventh orifice 237b that is an inlet for flushing purpose and an essentially tangential stator groove 238 extending over an angel α corresponding to the partition angel of the valve, all (except the first orifice 231b) being at a radial distance R from the stator face centre. However, it differs from the first embodiment in that the fifth and seventh orifices 235b and 237b are rotated the angle α counterclockwise (when viewing the inner stator face) with respect to their positions in the first embodiment.

The inner rotor face 212a of the rotor 212 of the second embodiment for cooperation with the stator 211 above is shown in FIG. 15. It is provided with a first groove 221, a second groove 222, a third groove 223 and a fourth groove 224.

As for the first embodiment, all rotor grooves end at essentially the same radial distance R from the center, except for one end of the first groove 221 that ends in the center of the rotor face 212a (coinciding with the rotary axis of the valve). The radial distance R for the rotor is the same as the corresponding radial distance R of the stator. The third and the fourth grooves 223 and 224 each extend over the angle α, which in the present embodiment is 30°. The first groove 221 is a straight groove from the center of the rotor face out towards the rim, with a length of R, and is parted from the nearest end of the second groove 222 by the angle 2α. The second groove 222, that extends over an angle of 4α, is bent inwards toward the centre to form a knee (or alternatively in an arcuate shape), thereby giving place for the third groove 223 that extends the angle α tangentially, starting from a position at an angle of 3α counterclockwise from the outer end of the first groove 221 when viewing the rotor face. The fourth groove 224 extends the angle α tangentially, starting from a position at an angle of 2α clockwise from the outer end of the first groove 221 when viewing the inner rotor face.

Similar to the first embodiment, different operational positions are obtainable when the stator and rotor faces are mated in rotational cooperation. These are shown in FIG. 16-20.

Figure 16:
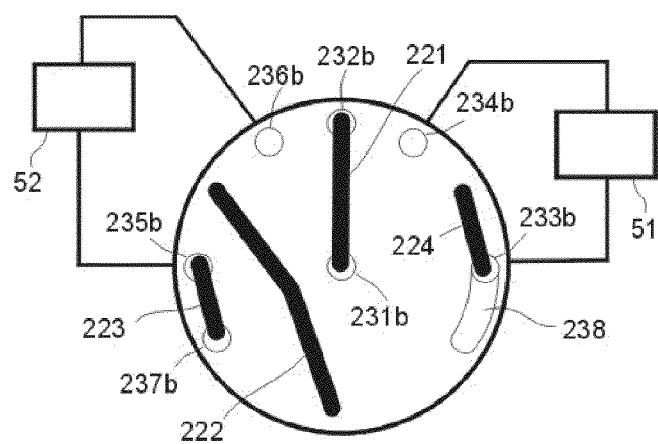
FIG. 16 is a schematic view of the second embodiment of the invention in a first position.

In the first rotary position of the rotor of the second valve embodiment, as shown in FIG. 16, the valve is useful to bypass both the first and the second component 51, 52. The flow enters the inlet port and goes via the first orifice 231b through the first rotor groove 221 and exits the valve through the outlet port via the second orifice 232b.

Figure 17:
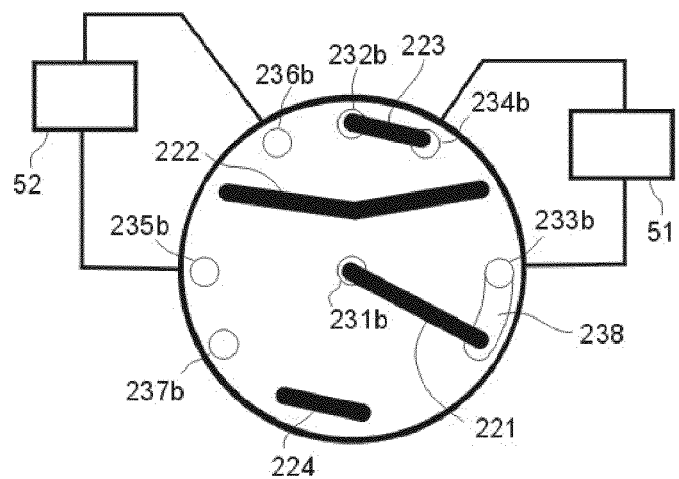
FIG. 17 is a schematic view of the second embodiment of the invention in a second position.

The second rotary position, as shown in FIG. 17, is obtained by rotating the rotor an angle of 4α clockwise (as seen from the view of FIG. 17) with respect to the first rotary position. The second position is useful to bypass the second component.

In the second rotary position the fluid that enters the inlet port and the first orifice 231b will pass through the first groove 221 and then the stator groove 238 to exit to the first component 51 via the third orifice 233b. After passing the first component 51, the flow returns to the valve via the fourth orifice 234b, passes the third rotor groove 223 and then exits the valve via the port connected with the second orifice 232b.

Figure 18:
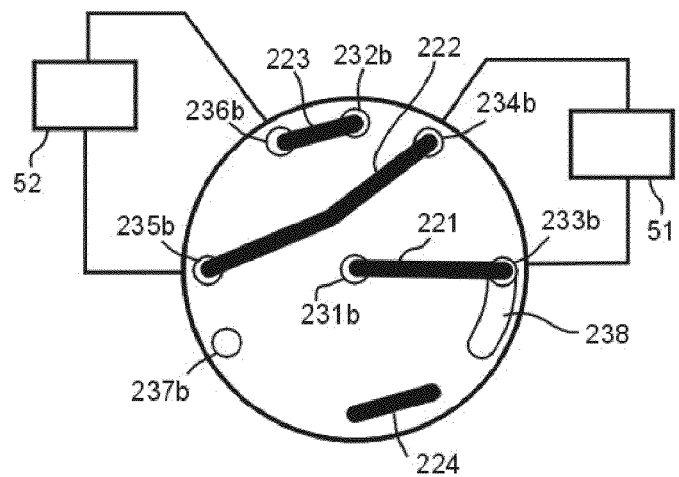
FIG. 18 is a schematic view of the second embodiment of the invention in a third position.

The third rotary position, as shown in FIG. 18, is obtained by rotating the rotor an angle of 3α clockwise (as seen from the view of FIG. 18) with respect to the first rotary position. In this position, the flow may pass both the first and the second components 51, 52.

In the third rotary position, the fluid enters via the first orifice 231b to pass through the first groove 221 and then exits to the first component 51 via the port connected with third orifice 233b. In this case, the stator groove 238 forms a short cul-de-sac that can be rinsed when the rotor is set to the second position, or to the fifth rotary position described below. After having passed the first component 51, the flow returns to the valve via the port connected with the fourth orifice 234b, passes the second groove 222 and then exits to the second component 52 via the port connected with the fifth orifice 235b. After passing the second component 52, the flow returns to the valve via the port connected with the sixth orifice 236b, passes the third rotor groove 223 and then exits the valve via the outlet port connected with the second orifice 232b.

Figure 19:
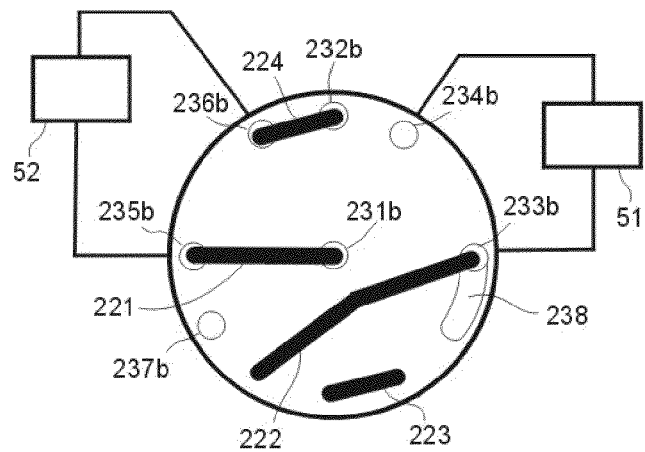
FIG. 19 is a schematic view of the second embodiment of the invention in a fourth position.

A fourth rotary position, as shown in FIG. 19, is obtained by rotating the rotor an angle of 3α counterclockwise (as seen from the view of FIG. 19) with respect to the first rotary position. The fourth position is useful to bypass the first component.

In the fourth rotary position, the fluid enters via the first orifice 231b and passes through the first groove 221 to exit to the second component 52 via the port connected with the fifth orifice 235b. After passing the second component 52, the flow returns to the valve via the sixth orifice 236b, passes the fourth rotor groove 224 and then exits the valve via the outlet port connected with the second orifice 232b.

Figure 20:
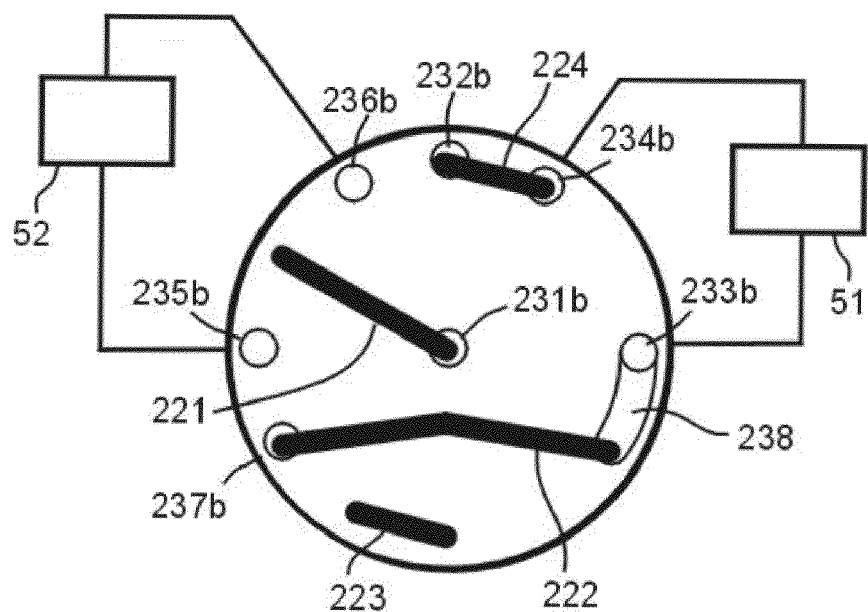
FIG. 20 is a schematic view of the second embodiment of the invention in a fifth position.

A fifth rotary position, as shown in FIG. 20, is obtained by rotating the rotor an angle 2α counterclockwise (as seen from the view of FIG. 20) with respect to the first rotary position. This position, that is optional, is useful for manual flushing of the first component 51 (such as during a calibration procedure for the first component 51 or for cleaning purpose).

In the fifth rotary position, a fluid is entered via the port in communication with the seventh orifice 237b, for example by using a syringe connected to the port. The fluid passes the second rotor groove 222 and the stator groove 238 to exit to the first component 51 via the port connected with the third orifice 233b. After having passed the first component 51, the flow returns to the valve via the port in communication with the fourth orifice 234b, passes the fourth rotor groove 224 and then exits the valve via the outlet port connected with the second orifice 232b.

Thus, with a valve of the second embodiment it is possible to selectively bypass the valve, connect the first component 51 in-line while bypassing the second component 52, connect the second component 52 in-line while bypassing the first component 51, or connect the first and second components 51 and 52 (in said order) in-line. In addition an optional flushing position is provided. This means that the second embodiment adds the possibility to connect the second component 52 in-line while bypassing the first component 51, as compared to the first embodiment described above.

Figure 21:
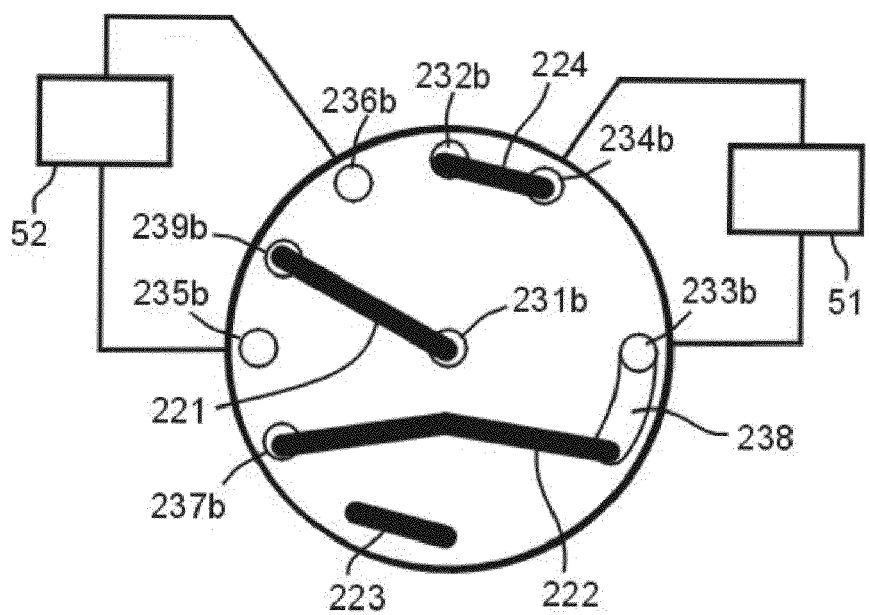
FIG. 21 is a schematic view of a modification of the second embodiment of the invention in a fifth position.

It should be noted that in this fifth position, without an additional outlet orifice, the first rotor groove 221 forms a stop for any flow from the fluid source via the first orifice 231b. This might be a disadvantage in a case where the user desires to use the fluid source also when the valve is in this fifth position. Therefore, in a modification of the second embodiment illustrated in FIG. 21, an additional outlet orifice 239b is provided between the fifth and sixth orifices 235b, 236b associated with the second component 52.

The modification consists of the addition of an additional outlet port in the stator, said port is in fluid communication with the additional outlet orifice 239b of the inner stator face. The additional outlet orifice 239b is situated between the fifth and sixth orifices 235b and 236b in such a way that it connects to the first rotor groove 221 when the rotor is in its fifth position, as described above. Thus, any flow entering the valve via the port associated with the first orifice 231b will pass the first groove 221 and then exit the valve via the additional outlet orifice 239b.

One specifically advantageous application of the invention is when a pH-sensor is the component that can be flushed, i.e. the second component in the first embodiment and the first component in the second embodiment. The feature of flushing the pH-sensor gives the advantage that the pH-sensor can be calibrated and stored in a storage solution without having to be demounted from its holder.

It should be noted that the fourth groove of both the first and second embodiment and the fifth groove of the first embodiment are optional and not necessary for the invention. However these grooves add additional suitable features to the invention as previously described.

As described above the exact position of the orifices need not to be according to the embodiment described above. What is important for the invention is that the different grooves reaches the specific orifices that should be reached in each rotation position described above.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A rotary valve for selectively connecting at least one component (51, 52) into a fluid path, the valve comprising a stator (111, 211) and a rotor (112, 212), said stator (111, 211) comprising a number of connection ports protruding into the stator and each ending in an orifice on an inner stator face (111*a*, 211*a*), which is a face of the stator making contact in a fluid tight manner with an inner rotor face (112*a*, 212*a*) of the rotor (112, 212), said inner rotor face (112*a*, 212*a*) being rotatably movable around a rotational axis (RA) relative to the inner stator face (111*a*, 211*a*), wherein said inner stator face (111*a*, 211*a*) comprises:
- a first orifice (131*b*, 231*b*) communicating with a first inlet port (131*a*) of the stator, said first orifice (131*b*, 231*b*) being positioned essentially centrally in the inner stator face (111*a*, 211*a*), which center coincides essentially with the rotary axis (RA) of the valve,
- a second orifice (132*b*, 232*b*) communicating with a second port (132*a*), being an outlet port of the stator,
- a third orifice (133*b*, 233*b*) communicating with a third port (133*a*) for a first fluid connection with a first component (51),
- a fourth orifice (134*b*, 234*b*) communicating with a fourth port (134*a*) for a second fluid connection with the first component (51),
- a fifth orifice (135*b*, 235*b*) communicating with a fifth port (135*a*) for a first fluid connection with a second component (52),
- a sixth orifice (136*b*, 236*b*) communicating with a sixth port (136*a*) for a second fluid connection with the second component (52),
- a generally tangentially extending stator groove (138, 238)

wherein said second, third, fourth, fifth, and sixth orifices (132*b*-136*b*, 232*b*-236*b*) and said stator groove (138, 238) are distributed substantially on a circle around the center of the inner stator face (111*a*, 211*a*), said circle having a radius (R), and further wherein
said inner rotor face (112*a*, 212*a*) comprises at least a first groove (121, 221), a second groove (122, 222), and a third groove (123, 223) so arranged that,
- in a first rotary position of the rotor the first groove (121, 221) connects the first orifice (131*b*, 231*b*) with the second orifice (132*b*, 232*b*);
- in a second rotary position of the rotor the first groove (121, 221) connects the first orifice (131*b*, 231*b*) with the third orifice (133*b*, 233*b*) via the stator groove (138, 238), and the third groove (123, 223) connects the fourth orifice (134*b*, 234*b*) with the second orifice (132*b*, 232*b*); and
- in a third rotary position of the rotor the first groove (121, 221) connects the first orifice (131*b*, 231*b*) with the third orifice (133*b*, 233*b*), the second groove (122, 222) connects the fourth orifice (134*b*, 234*b*) with the fifth orifice (135*b*, 235*b*), and the third groove (123, 223) connects the sixth orifice (136*b*, 236*b*) with the second orifice (132*b*, 232*b*).

2. The rotary valve of claim 1,
wherein said inner rotor face (212*a*) further comprises a fourth groove (224), so arranged that,
- in a fourth rotary position of the rotor the first groove (221) connects the first orifice (231*b*) with the fifth orifice (235*b*), and said fourth groove (125) connects the sixth orifice (236*b*) with the second orifice (232*b*).

3. The rotary valve of claim 2,
wherein said inner stator face (211*a*) further comprises
a seventh orifice (237*b*) communicating with a seventh port, being an inlet port to the valve,
and said second groove (222) and said fourth groove (224) being so arranged that,
- in a fifth rotary position of the rotor, the second groove (222) connects the seventh orifice (237*b*) with the third orifice (233*b*) via the stator groove (238) and the fourth groove (224) connects the fourth orifice (234*b*) with the second orifice (232*b*).

4. The rotary valve of claim 3,
wherein said inner stator face (211*a*) further comprises
an additional outlet orifice (239*b*) communicating with an additional outlet port, and in that
the first groove (221) is so arranged that
- in the fifth rotary position, the first groove (221) connects the first orifice (231*b*) with the additional outlet orifice (239*b*).

5. The rotary valve of claim 1,
wherein said inner stator face (111*a*) further comprises
a seventh orifice (137*b*) communicating with a seventh port (137*a*) being an inlet port to the valve, and
said inner rotor face (112*a*) further comprises a fourth groove (124) and a fifth groove (125), so arranged that,
- in a fourth rotary position of the rotor the fifth groove (125) connects the seventh orifice (137*b*) with the fifth orifice (135*b*) and the fourth groove (124) connects the sixth orifice (136*b*) with the second orifice (132*b*).

6. The rotary valve of claim 5,
wherein said inner stator face (111*a*) further comprises
an additional outlet orifice (139*b*) communicating with an additional outlet port, and in that
the first groove (121) is so arranged that
- in the fourth rotary position, the first groove (121) connects the first orifice (131*b*) with the additional outlet orifice (139*b*).

* * * * *